United States Patent
Zheng et al.

(10) Patent No.: US 12,190,568 B2
(45) Date of Patent: Jan. 7, 2025

(54) METHODS AND APPARATUSES FOR TRAINING MAGNETIC RESONANCE IMAGING MODEL

(71) Applicant: SHENZHEN INSTITUTES OF ADVANCED TECHNOLOGY, Guangdong (CN)

(72) Inventors: Hairong Zheng, Guangdong (CN); Xin Liu, Guangdong (CN); Na Zhang, Guangdong (CN); Zhanli Hu, Guangdong (CN); Qihang Chen, Guangdong (CN); Dong Liang, Guangdong (CN); Yongfeng Yang, Guangdong (CN)

(73) Assignee: SHENZHEN INSTITUTES OF ADVANCED TECHNOLOGY, Shenzhen (CN)

( * ) Notice: Subject to any disclaimer, the term of this patent is extended or adjusted under 35 U.S.C. 154(b) by 386 days.

(21) Appl. No.: 17/889,189

(22) Filed: Aug. 16, 2022

(65) Prior Publication Data

US 2023/0047647 A1 Feb. 16, 2023

Related U.S. Application Data

(63) Continuation of application No. PCT/CN2020/077011, filed on Feb. 27, 2020.

(30) Foreign Application Priority Data

Feb. 24, 2020 (CN) .......................... 202010113026.2

(51) Int. Cl.
*G06V 10/774* (2022.01)
*A61B 5/055* (2006.01)
(Continued)

(52) U.S. Cl.
CPC ............ *G06V 10/774* (2022.01); *A61B 5/055* (2013.01); *G06T 11/00* (2013.01); *G06V 10/42* (2022.01); *G06T 2210/41* (2013.01)

(58) Field of Classification Search
CPC .. G06V 10/774; G06V 10/42; G06V 2201/03; G06V 10/82; A61B 5/055;
(Continued)

(56) References Cited

U.S. PATENT DOCUMENTS

2020/0058126 A1  2/2020  Wang et al.

FOREIGN PATENT DOCUMENTS

CN   106560848         4/2017
CN   108577840 A  *   9/2018
(Continued)

OTHER PUBLICATIONS

The international search report of the corresponding PCT Application No. PCT/CN2020/077011 mailed on Nov. 27, 2020 along with English translation thereof.
(Continued)

*Primary Examiner* — Samir A Ahmed
(74) *Attorney, Agent, or Firm* — NZ CARR LAW OFFICE

(57) ABSTRACT

Methods and apparatuses for training a magnetic resonance imaging model, electronic devices and computer readable storage media are provided. A method may include: acquiring a magnetic resonance image data set; constructing a ring deep neural network to be trained; inputting an under-sampled magnetic resonance image and a full-sampled magnetic resonance image respectively to two neural networks included in the ring deep neural network, to generate respective simulated magnetic resonance images; inputting a first simulated full-sampled magnetic resonance image and the full-sampled magnetic resonance image to a pre-constructed
(Continued)

first simulated magnetic resonance image class discrimination model, to obtain a first discrimination result indicating whether or not the first simulated full-sampled magnetic resonance image is of a simulated magnetic resonance image class; and adjusting a network parameter of the ring deep neural network based on a preset loss function, to obtain a trained magnetic resonance imaging model.

14 Claims, 7 Drawing Sheets

(51) Int. Cl.
 *G06T 11/00* (2006.01)
 *G06V 10/42* (2022.01)
(58) Field of Classification Search
 CPC ... A61B 5/7264; G06T 11/00; G06T 2210/41; G06N 3/045; G06N 3/08
 See application file for complete search history.

(56) References Cited

FOREIGN PATENT DOCUMENTS

| | | | |
|---|---|---|---|
| CN | 109325985 | | 2/2019 |
| CN | 109523584 | | 3/2019 |
| CN | 109544652 | | 3/2019 |
| CN | 109658352 | | 4/2019 |
| CN | 109671129 A | * | 4/2019 |
| CN | 109712208 | | 5/2019 |
| CN | 110728732 | | 1/2020 |

OTHER PUBLICATIONS

A paper entitled "Model-based Deep Medical Imaging: the roadmap of generalizing iterative reconstruction model using deep learning" published on Jun. 19, 2019.

* cited by examiner

METHODS AND APPARATUSES FOR TRAINING MAGNETIC RESONANCE IMAGING MODEL

CROSS REFERENCE TO RELATED APPLICATIONS

This application is a continuation of International Application No. PCT/CN2020/077011, filed on Feb. 27, 2020, which claims priority to Chinese Patent Application No. 202010113026.2, filed on Feb. 24, 2020. The disclosures of the aforementioned applications are hereby incorporated by reference in their entireties.

TECHNICAL FIELD

The present disclosure relates to computer technologies, and in particular, to methods and apparatuses for training a magnetic resonance imaging model, electronic devices and computer-readable storage media.

BACKGROUND

Magnetic Resonance Imaging (MM) technology may be used to reconstruct human tissue images by means of nuclear magnetic resonance phenomenon and provide rich information on human tissue images without any ionizing damage to the human body, and thus has been widely used in clinical medical examination.

However, the speed of imaging by the MRI technology is relatively low due to the long time for image data acquisition. Thus, many artifacts may be introduced into the generated image due to the physiological movement of the subject during the imaging process, which may deteriorate image quality and thereby affect clinical diagnosis.

In order to reduce artifacts in the generated image, it is necessary to increase the imaging speed, that is, to shorten the time for image data acquisition by Mill. Currently, the way to shorten the time for image data acquisition by MRI mainly consists in reducing the amount of image data to be acquired, such as regular under-sampling based on partial k-space, random under-sampling based on Compressed Sensing (CS) theory, Radial and Spiral under-sampling based on non-Cartesian sampling trajectories, or the like. However, the reduction in the amount of image data to be acquired may inevitably reduce the clarity of the image.

Recently, deep learning methods, such as convolutional neural network, U-net convolutional neural network, residual convolutional neural network, or the like, have been applied to the fast magnetic resonance imaging, where high-quality MRI images can be quickly reconstructed by using a trained neural network with a small amount of image data acquired, which have great application potential.

At present, the adopted deep learning methods mainly achieve imaging by learning the mapping from under-sampled image data to full-sampled image data. However, such learning methods have relatively low learning efficiency and may generate images of relatively low quality.

SUMMARY

The embodiments of the present disclosure provide methods and apparatuses for training a magnetic resonance imaging model, electronic devices and computer-readable storage media, so as to solve the problem that the deep learning methods adopted in the relevant art have relatively low learning efficiency and may generate images of relatively low quality.

The embodiments of the present disclosure adopt the following technical solutions:

A method for training a magnetic resonance imaging model, comprising:
  acquiring a magnetic resonance image data set comprising an under-sampled magnetic resonance image and a full-sampled magnetic resonance image;
  constructing a ring deep neural network to be trained, wherein the ring deep neural network comprises a first neural network at a first side, a second neural network at a second side, and two input ports respectively for the under-sampled magnetic resonance image and the full-sampled magnetic resonance image,
  wherein the first neural network is configured to generate a first simulated full-sampled magnetic resonance image based on the under-sampled magnetic resonance image and generate a second simulated full-sampled magnetic resonance image based on a first simulated under-sampled magnetic resonance image generated by the second neural network, and the second neural network is configured to generate the first simulated under-sampled magnetic resonance image based on the full-sampled magnetic resonance image and generate a second simulated under-sampled magnetic resonance image based on the first simulated full-sampled magnetic resonance image generated by the first neural network;
  inputting the under-sampled magnetic resonance image and the full-sampled magnetic resonance image respectively to the first neural network and the second neural network via the two input ports, to generate respective simulated magnetic resonance images comprising the first simulated under-sampled magnetic resonance image, the first simulated full-sampled magnetic resonance image, the second simulated under-sampled magnetic resonance image and the second simulated full-sampled magnetic resonance image;
  inputting the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class;
  inputting the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class; and
  adjusting a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

A method for generating a magnetic resonance image based on the method for training the magnetic resonance imaging mode, the method for generating a magnetic resonance image comprising:
  acquiring under-sampled image data; and
  inputting the under-sampled image data to the trained magnetic resonance imaging model, to generate a magnetic resonance image.

An apparatus for training a magnetic resonance imaging model, comprising:
  an acquisition module configured to acquire a magnetic resonance image data set comprising an under-sampled magnetic resonance image and a full-sampled magnetic resonance image;
  a construction module configured to construct a ring deep neural network to be trained, wherein the ring deep neural network comprises a first neural network at a first side, a second neural network at a second side, and two input ports respectively for the under-sampled magnetic resonance image and the full-sampled magnetic resonance image, wherein the first neural network is configured to generate a first simulated full-sampled magnetic resonance image based on the under-sampled magnetic resonance image and generate a second simulated full-sampled magnetic resonance image based on a first simulated under-sampled magnetic resonance image generated by the second neural network, and the second neural network is configured to generate the first simulated under-sampled magnetic resonance image based on the full-sampled magnetic resonance image and generate a second simulated under-sampled magnetic resonance image based on the first simulated full-sampled magnetic resonance image generated by the first neural network;
  a generation module configured to input the under-sampled magnetic resonance image and the full-sampled magnetic resonance image respectively to the first neural network and the second neural network via the two input ports, to generate respective simulated magnetic resonance images comprising the first simulated under-sampled magnetic resonance image, the first simulated full-sampled magnetic resonance image, the second simulated under-sampled magnetic resonance image and the second simulated full-sampled magnetic resonance image;
  a first discrimination module configured to input the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class;
  a second discrimination module configured to input the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class; and
  a parameter adjustment module configured to adjust a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

A magnetic resonance imaging apparatus based on the apparatus for training the magnetic resonance imaging model, the magnetic resonance imaging apparatus comprising:
  an image data acquisition module configured to acquire under-sampled image data;
  a generation module configured to input the under-sampled image data to the trained magnetic resonance imaging model, to generate a magnetic resonance image.

An electronic device, comprising: a storage, a processor and a computer program stored in the storage and executable on the processor, the computer program, when executed by the processor, performing the method for training the magnetic resonance imaging model.

A computer readable storage medium storing a computer program that, when executed by a processor, causes the processor to implement the method for training the magnetic resonance imaging model.

At least one of the technical solutions based on the embodiments of the present disclosure can achieve the following beneficial effects:

Since only the mapping relationship of a single image generation direction (for example, from an under-sampled image to a full-sample image) is learned, the generated Mill image may have a large deviation from the actual MRI image, and the learning efficiency of the neural network is not high. By means of the constructed ring deep neural network in the present disclosure, during the process of training, not only the mapping relationship of the image generation direction from the under-sampled magnetic resonance image to the full-sampled magnetic resonance image can be learned, but also, since the addition of the second neural network in the opposite direction of the image generation, the mapping relationship in the opposite direction from the full-sampled magnetic resonance image to the under-sampled magnetic resonance image can also be learned, thereby the mapping relationship learned by the first neural network can be corrected, so that the first neural network can form a correct mapping in the desired image generation direction, thereby reducing the deviation between the generated MM image and the actual Mill image, improving the quality of the MM images generated by the magnetic resonance imaging model, and improving the learning ability and learning efficiency of the neural network.

On the other hand, by using the first simulated magnetic resonance image class discrimination model and the second simulated magnetic resonance image class discrimination model, the generated first simulated full-sampled magnetic resonance image and the first simulated under-sampled magnetic resonance image are also be discriminated, and the discrimination results are fed back to the training of the ring deep neural network through the loss function. It is expected to achieve the purpose of making the simulated magnetic resonance image discrimination model misjudge the simulated magnetic resonance image generated by the ring deep neural network as a non-simulated magnetic resonance image, so that the MM image generated by the trained magnetic resonance imaging model is as close as possible to the actual MRI image, thereby further improving the quality of the MRI image generated by the magnetic resonance imaging model.

BRIEF DESCRIPTION OF DRAWINGS

The accompanying drawings are used to provide further understanding of the present disclosure and constitute a part of the present disclosure. The schematic embodiments and their descriptions of the present disclosure are used to explain the present disclosure and are not intended to limit the present disclosure. In the drawings.

DETAILED DESCRIPTION

In order to make the objectives, technical solutions and advantages of the present disclosure more clear, the technical solutions of the present disclosure will be clearly and completely described below with reference to the specific embodiments of the present disclosure and corresponding drawings. Obviously, the described embodiments are only a part of the embodiments of the present disclosure, but not all of the embodiments. Based on the embodiments in the present disclosure, all other embodiments obtained by those skilled in the art without creative work fall within the protection scope of the present disclosure.

The technical solutions provided by the embodiments of the present disclosure will be described in detail below with reference to the drawings.

In recent years, deep learning methods such as convolutional neural network, U-net convolutional neural network or Residual convolutional neural network have been applied to the field of fast magnetic resonance imaging, by which methods high-quality MRI images can be quickly reconstructed by using a trained neural network under the condition of collecting a small amount of image data, and which methods are a fast magnetic resonance image generation method with great application potential.

At present, the deep learning methods adopted mainly learn the mapping relationship from under-sampled image data to full-sampled image data to achieve imaging, but such learning methods have low learning efficiency and relatively low quality of generated images.

Figure 1:
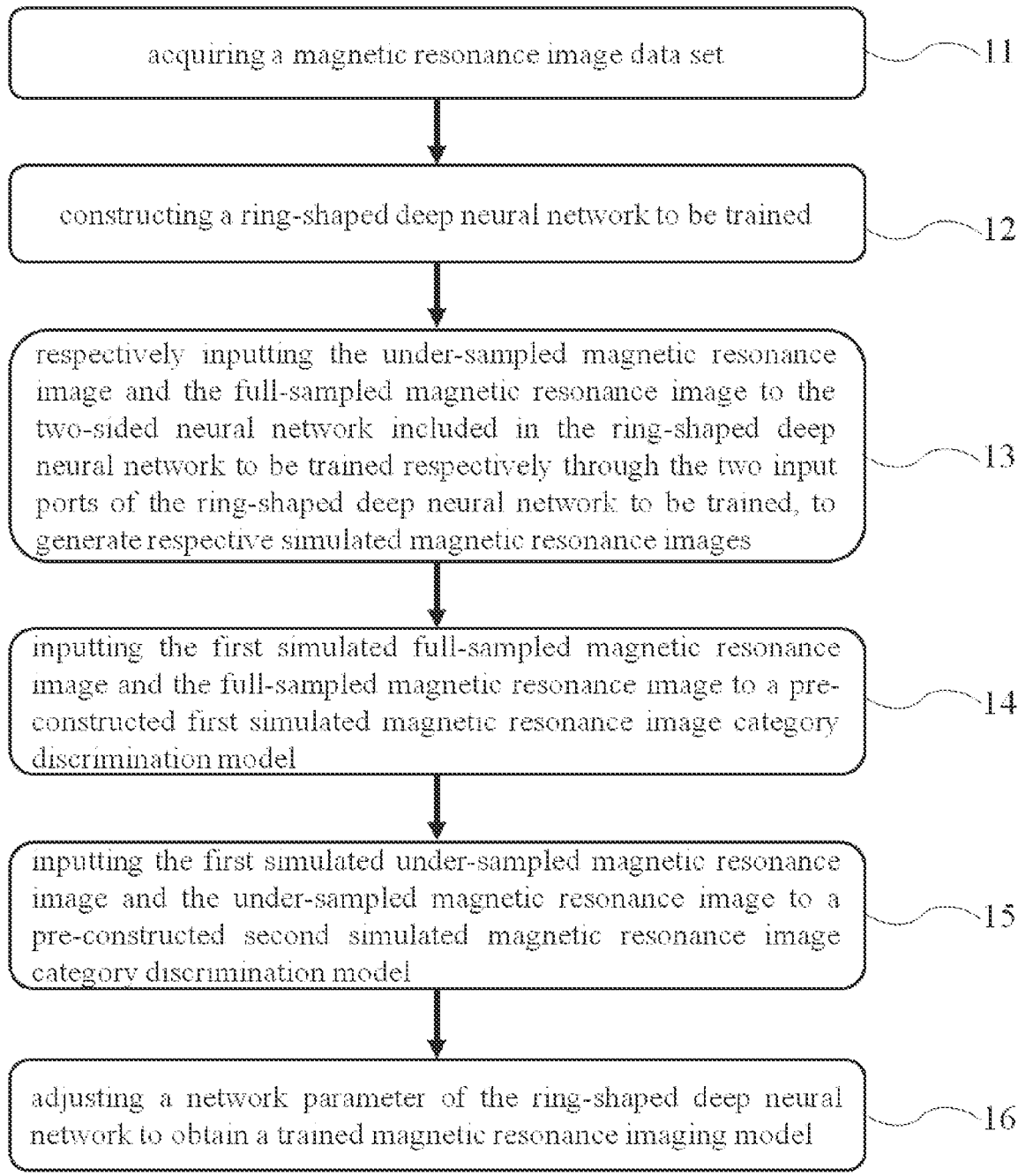
FIG. 1 is a schematic flowchart of a method for training a magnetic resonance imaging model according to an embodiment of the present disclosure.

In order to solve the above technical problems, the embodiments of the present disclosure provide a method for training a magnetic resonance imaging model, for improving the learning efficiency of the neural networks and the quality of the generated magnetic resonance images. The execution subject of the method comprises, but is not limited to, intelligent electronic devices such as servers, personal computers, notebook computers, tablet computers, and smart phones that can execute predetermined processing procedures such as numerical calculations and/or logical calculations by running predetermined programs and instructions. Wherein, the servers may be a single network server or a server group consisting of multiple network servers, or a cloud consisting of a large number of computers and network servers based on Cloud Computing. In the embodiments of the present disclosure, the execution subject of the method is not limited. A schematic flowchart of the method is shown in FIG. 1, which comprises the following steps:

Step 11: acquiring a magnetic resonance image data set.

The magnetic resonance image data set herein may comprise an under-sampled magnetic resonance image and a full-sampled magnetic resonance image.

In practical applications, the full-sampled magnetic resonance image may be derived from magnetic resonance image data actually collected by a magnetic resonance imaging device. The under-sampled magnetic resonance image may be magnetic resonance image data formed by extracting partial sampling point data from the full-sampled magnetic resonance image. Wherein, extracting partial sampling point data may be extraction based on k-space regular, or may be random extraction based on Compressed Sensing theory, which is not limited in the present disclosure.

In practical applications, after extracting partial sampling point data from the full-sampled magnetic resonance image to generate the under-sampled magnetic resonance image, the method may further comprise establishing a matching relationship between the under-sampled magnetic resonance image and the full-sampled magnetic resonance image, so that the full-sampled magnetic resonance image and under-sampled magnetic resonance image in the magnetic resonance image data set are correspondingly matched, facilitating the training of the neural network later.

Step 12: constructing a ring deep neural network to be trained.

Considering the problems that the deep learning methods adopted in the relevant art only learn the mapping relationship of a single image generation direction to realize imaging, so that the quality of the generated magnetic resonance images is relatively low and the learning efficiency of the neural network is not high, in the embodiments of the present disclosure, the above-mentioned technical problems are solved by constructing a ring deep neural network to be trained. Wherein, a constructed ring deep neural network may comprise a first neural network at a first side, a second neural network at a second side, and two input ports.

In practical applications, the two input ports may be configured to respectively input an under-sampled magnetic resonance image and a full-sampled magnetic resonance image, where the under-sampled magnetic resonance image and full-sampled magnetic resonance image may be acquired by Step 11.

Figure 2:
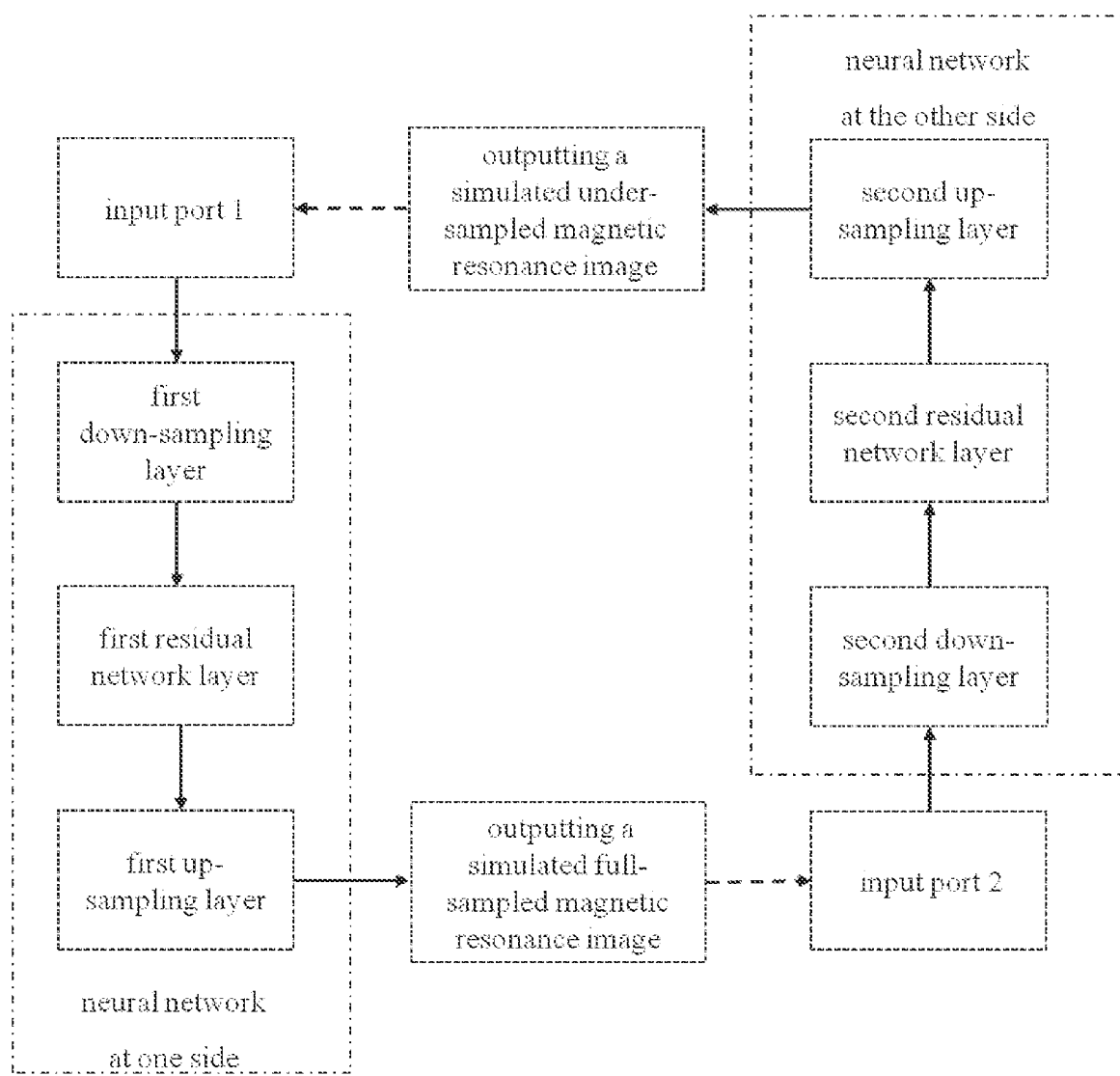
FIG. 2 is a schematic structure diagram of a ring deep neural network according to an embodiment of the present disclosure.

In one or more embodiments of the present disclosure, a schematic structure diagram of a ring deep neural network as shown in FIG. 2, the first neural network of the ring deep neural network may comprise a first down-sampling layer, a first residual network layer, and a first up-sampling layer; and the second neural network may comprise a second down-sampling layer, a second residual network layer and a second up-sampling layer.

Wherein, the first down-sampling layer, the first up-sampling layer, the second up-sampling layer and the second down-sampling layer may respectively comprise at least one convolutional layer, and each convolutional layer in the at least one convolutional layer adopts serial connection, that is, an output map of the previous convolutional layer can be used as an input map of the next convolutional layer. Each convolutional layer can perform convolution processing on the input map, and each convolutional layer can comprise at least one convolution kernel, and each convolution kernel is used to indicate a weight matrix in one convolution operation. It should be noted that the above input map and output map may both refer to feature maps.

Figure 3:
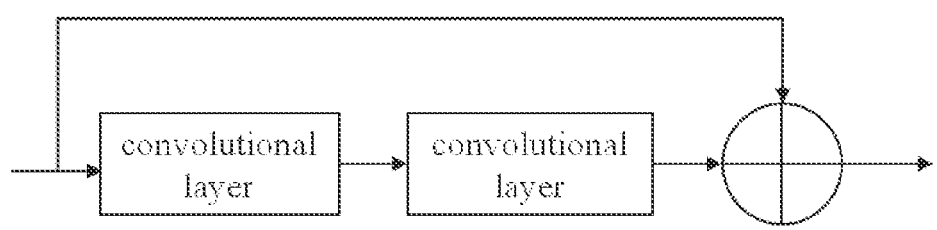
FIG. 3 is a schematic structure diagram of a residual block according to an embodiment of the present disclosure.

The first residual network layer and the second residual network layer may respectively comprise at least one residual block. Wherein, the schematic structure diagram of each residual block may be shown in FIG. 3, and each residual block may be specifically composed of two-layer convolutional layers plus skip connections. Wherein, the two-layer convolutional layers can be used to extract deep-level image features, and the skip connections are used to directly transfer low-level image features backwards, and combine with the deep-level image features, which can improve the learning ability and stability of the neural network, and avoiding the degradation of the training effect of the relatively deeper neural network due to the increase of depth.

Figure 4:
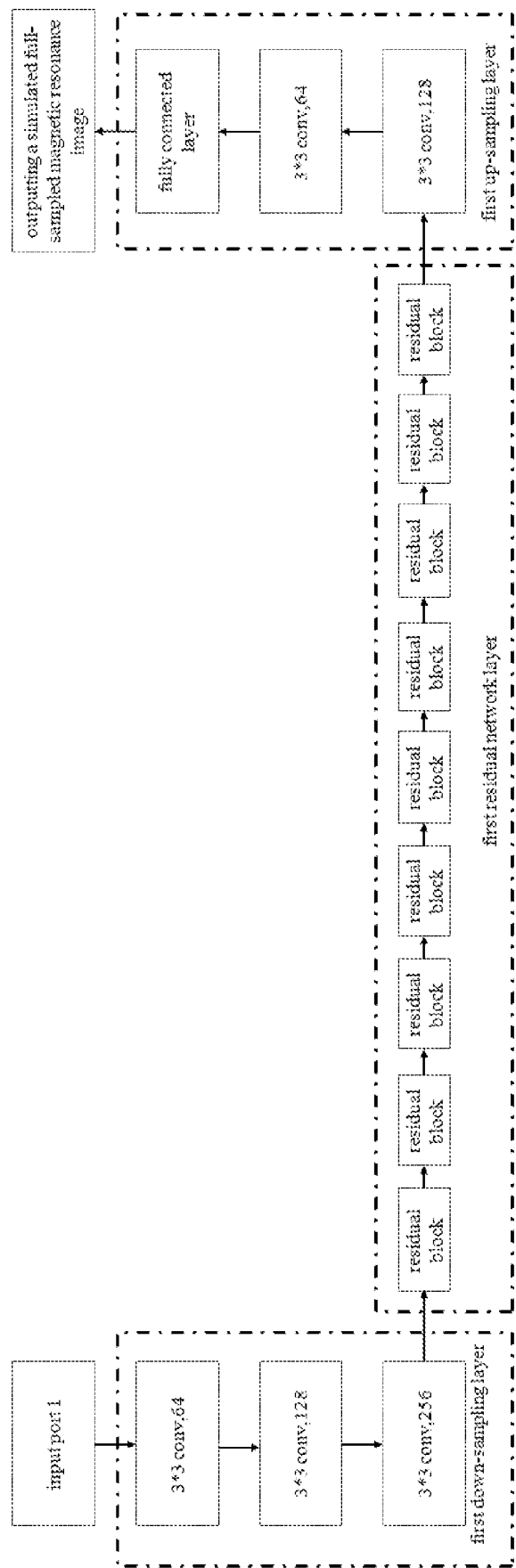
FIG. 4 is a schematic structure diagram of a first neural network according to an embodiment of the present disclosure.

As shown in FIG. 4 is a specific schematic structure diagram of a first neural network of an exemplary deep ring deep neural network given in an embodiment of the present disclosure.

In the first neural network, the first down-sampling layer and the first up-sampling layer respectively comprise 3 convolution layers, and the first residual network layer may comprise 9 residual blocks. In FIG. 4, the number and size of convolution kernels of each convolution layer are also shown, for example, "conv, 64" indicates that there are 64 convolution kernels in this convolution layer, and "3*3" indicates that the convolution kernel adopts a small convolution kernel with a size of 3*3, and the number and size of convolution kernels of the remaining convolutional layers will not be described.

The first convolutional layer of the first down-sampling layer can be used to perform convolution processing on pixel values of an input magnetic resonance image (for example, perform convolution processing on the pixel values of the under-sampled magnetic resonance image) to obtain a feature map output by the first convolutional layer, the output feature map is used as an input map of the following second convolutional layer, and so on, the output map of the second convolutional layer is used as the input map of the third convolutional layer.

In practical applications, the number of feature maps output by each convolutional layer can be the same as the number of convolution kernels of the convolutional layer. For example, as shown in FIG. 4, the number of feature maps output by the first convolutional layer of the first down-sampling layer is 64, the number of feature maps output by the second convolutional layer of the first down-sampling layer is 128, and the number of feature maps output by the third convolutional layer of the first down-sampling layer is 256. As the number of convolution kernels in each convolutional layer is doubled, the depth of extracting image features is doubled, and the size of the feature map output by each convolutional layer is reduced by half.

Each feature map output by the first down-sampling layer can represent the local features of the input under-sampled magnetic resonance image, and then by passing through the first residual network layer, the feature map output by the first down-sampling layer can be subjected to residual processing. It can be understood that, by passing through each residual block of the first residual network, a residual calculation is performed on each feature map representing local features layer by layer to further extract deeper image features, so that the extracted local features are more significant and the learning ability of neural networks is improved.

The two convolutional layers of the first up-sampling layer can combine the feature maps layer by layer after residual processing by the first residual network layer, for example, 256 feature maps are combined into 128 feature maps, 128 feature maps are combined into 64 feature maps, and correspondingly enlarge the size of the feature maps layer by layer. Then connect each feature map through the fully connected layer, and output the generated simulated magnetic resonance image. For example, input 64 feature maps combined by the two convolutional layers into the fully connected layer to connect the 64 feature maps, and output the generated first simulated full-sampled magnetic resonance image.

Figure 5:
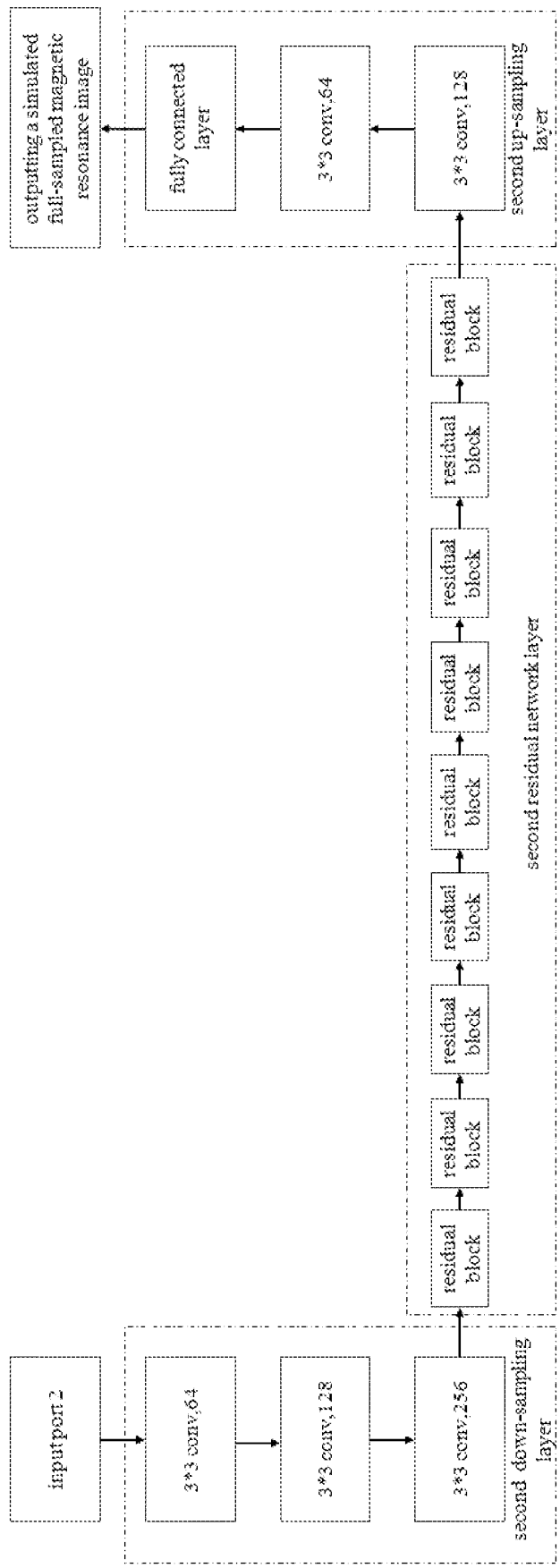
FIG. 5 is a schematic structure diagram of a second neural network according to an embodiment of the present disclosure.

For the network structure of the second neural network of the ring deep neural network, it can be the same as the network structure of the first neural network, for example, a specific schematic structure diagram of the second neural network is shown in FIG. 5, in which the number of convolution layers, the number of convolution kernels, and the size of the convolution kernels can refer to the explanation of the first neural network shown in FIG. 4, which will not be repeated here.

It should be noted that the above-mentioned exemplary ring deep neural network is a specific implementation of constructing a ring deep neural network provided by the embodiments of the present disclosure, and does not represent all implementations of the embodiments of the present disclosure. The number of convolutional layers, the number of residual blocks, the number of convolution kernels, and the size of the convolution kernels included in the ring deep neural network can be set according to actual needs, which is not limited in the present disclosure.

Step 13: inputting the under-sampled magnetic resonance image and the full-sampled magnetic resonance image respectively to the first neural network and the second neural network via the two input ports, to generate respective simulated magnetic resonance images;

The under-sampled magnetic resonance image and the full-sampled magnetic resonance image here can be acquired by Step 11. The ring deep neural network to be trained here can be constructed by Step 12.

The respective simulated magnetic resonance images here can comprise: a first simulated under-sampled magnetic resonance image, a first simulated full-sampled magnetic resonance image, a second simulated under-sampled magnetic resonance image and a second simulated full-sampled magnetic resonance image.

In order to facilitate the understanding of the process of generating respective simulated magnetic resonance images, here is an explanation in conjunction with the ring deep neural network shown in FIG. 2:

For the under-sampled magnetic resonance image: input the under-sampled magnetic resonance image via an input port 1 to the first neural network, and output a first simulated full-sampled magnetic resonance image, and then input the first simulated full-sampled magnetic resonance image via an input port 2 to the second neural network, to generate a second simulated under-sampled magnetic resonance image;

For the full-sampled magnetic resonance image: input the full-sampled magnetic resonance image via the input port 2 to the second neural network and output a first simulated under-sampled magnetic resonance image, and then input the first simulated under-sampled magnetic resonance image via the input port 1 to the first neural network, to generate a second simulated full-sampled magnetic resonance image.

From this, it can be understood that the respective roles of the first neural network and the second neural network comprising: the first neural network is configured to generate a first simulated full-sampled magnetic resonance image based on the under-sampled magnetic resonance image and generate a second simulated full-sampled magnetic resonance image based on the first simulated under-sampled magnetic resonance image generated by the second neural network; the second neural network is configured to generate a first simulated under-sampled magnetic resonance image based on the full-sampled magnetic resonance image and generate a second simulated under-sampled magnetic resonance image based on the first simulated full-sampled magnetic resonance image generated by the first neural network.

In the embodiments of the present disclosure, in order to further understand the process of generating respective simulated magnetic resonance images by the first and second neural networks, combined with the network structure of the first and second neural networks shown in FIG. 2, the process of generating respective simulated magnetic resonance images may specifically comprise:

For the under-sampled magnetic resonance image: input the under-sampled magnetic resonance image to the first neural network via an input port 1, extract a first feature map of the under-sampled magnetic resonance image through the first down-sampling layer, perform the residual processing on the first feature map through a first residual network to obtain the first feature map subjected to the residual processing, and then generate a first simulated full-sampled magnetic resonance image based on the first feature map subjected to the residual processing through a first up-sampling layer; and then input the first simulated full-sampled magnetic resonance image to the second neural network via an input port 2, extract a fourth feature map of the first simulated full-sampled magnetic resonance image through a second down-sampling layer, perform residual processing on the fourth feature map through a second residual network layer to obtain the fourth feature map subjected to the residual processing, and then generate a second under-sampled magnetic resonance image based on the fourth feature map subjected to the residual processing through a second up-sampling layer.

For the full-sampled magnetic resonance image: input the full-sampled magnetic resonance image to the second neural network via the input port 2, extract a third feature map of the full-sampled magnetic resonance image through a second down-sampling layer, perform the residual processing on the third feature map through a second residual network to obtain the third feature map subjected to the residual processing, and then generate a first simulated under-sampled magnetic resonance image based on the third feature map subjected to the residual processing through a second up-sampling layer; and then input the first simulated under-sampled magnetic resonance image to the first neural network via an input port 1, extract a second feature map of the first simulated under-sampled magnetic resonance image through a first down-sampling layer, perform residual processing on the second feature map through the first residual network layer to obtain the second feature map subjected to the residual processing, and then generate a second simulated full-sampled magnetic resonance image based on the second feature map subjected to the residual processing through a first up-sampling layer.

Step 14: inputting the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class.

The first simulated full-sampled magnetic resonance image here can be generated by Step 13. The full-sampled magnetic resonance image here can be acquired by Step 11.

In practical applications, considering that during the training process, there may be a deviation between the first simulated full-sampled magnetic resonance image generated from the under-sampled magnetic resonance image and the full-sampled magnetic resonance image that matches the under-sampled magnetic resonance image, the quality of the magnetic resonance images generated by the ring deep neural network can be further improved, if this deviation can be fed back into the training of the ring deep neural network.

However, the magnitude of this deviation cannot be measured in the ring deep neural network constructed in Step 12. Therefore, in the embodiments of the present disclosure, by pre-constructing the first simulated magnetic resonance image class discrimination model, it is possible to discriminate whether or not the generated first simulated full-sampled magnetic resonance image is of a simulated magnetic resonance image class, and obtain a first discrimination result, so that the first discrimination result can be fed back to the training of the ring deep neural network through a preset loss function, that is, the deviation existing between the first simulated full-sampled magnetic resonance image and the full-sampled magnetic resonance image is fed back to the training of the ring deep neural network.

Figure 6:
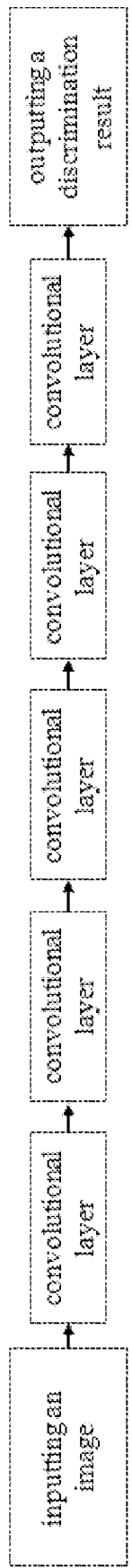
FIG. 6 is a schematic structure diagram of a simulated magnetic resonance image class discrimination model according to an embodiment of the present disclosure.

In the embodiments of the present disclosure, the pre-constructed first simulated magnetic resonance image class discrimination model may be constructed based on a convolutional neural networks (CNN), for example, the one shown in FIG. 6 may be a schematic structure diagram of the first simulated magnetic resonance image class discrimination model. Of course, other types of neural network construction can also be used, which is not limited in the present disclosure.

In practical applications, in the training process of the ring deep neural network, in order to enable the first simulated magnetic resonance image class discrimination model to accurately output the first discrimination result, it can be understood that, making the first simulated magnetic resonance image class discrimination model as much as possible that the first simulated full-sampled magnetic resonance image is a simulated magnetic resonance image class, in one or more embodiments of the present disclosure, for the pre-constructed first simulated magnetic resonance image class discrimination model, the model parameters of the first simulated magnetic resonance image class discrimination model may be adjusted through a fourth loss function, so that the first simulated magnetic resonance image class discrimination model accurately outputs the first discrimination result.

The fourth loss function can be:

$$L_4 = \{E_x[\text{MSE}(D_d(G_{s-d}(x)), 0] + E_y[\text{MSE}(D_d(y), 1]\}/2$$

wherein x represents the under-sampled magnetic resonance image, y represents the full-sampled magnetic resonance image, $G_{s-d}(x)$ represents the first simulated full-sampled magnetic resonance image, $D_d$ represents the first simulated magnetic resonance image class discrimination model, $D_d(G_{s-d}(x))$ represents the first discrimination result, MSE represents a mean square error (MSE) function, and $E_x$ represents a mathematical expectation of a first function whose input is the under-sampled magnetic resonance image; $D_d(y)$ represents a result of class discrimination with respect to the full-sampled magnetic resonance image by the first simulated magnetic resonance image class discrimination model; $E_y$ represents the mathematical expectation of a second function whose input is the full-sampled magnetic resonance image.

Adjusting the model parameters based on the fourth loss function may specifically comprise: calculating a loss value of the discrimination result of the first simulated magnetic resonance image class discrimination model through the fourth loss function, and feeding back the loss value to the first simulated magnetic resonance image class discrimination model by means of back propagation to adjust the model parameters.

In practical applications, since the input data of the first simulated magnetic resonance image class discrimination model comprises the first simulated full-sampled magnetic resonance image, and the first simulated full-sampled magnetic resonance image may be generated by the first neural network of the ring deep neural network, it can be considered that the first simulated magnetic resonance image class discrimination model and the ring deep neural network can be trained simultaneously. The training effects of the two are opposite, that is, training the ring deep neural network is expected to achieve the purpose of making the first simulated magnetic resonance image class discrimination model discriminate the first simulated full-sampled magnetic resonance image as a non-simulated magnetic resonance image class, while training the first simulated magnetic resonance image class discrimination model is expected to improve the accuracy of the discrimination model, so as to discriminate the first simulated full-sampled magnetic resonance image as the simulated magnetic resonance image class as much as possible. Since the first discrimination result output by the first magnetic resonance image discrimination model can be fed back to the training of the ring deep neural network through the preset loss function, the discrimination accuracy of the first simulated magnetic resonance image class discrimination model can also be improved, that is, the accuracy of the output first discrimination result can also be improved, also be equivalent to promoting the improvement of the quality of the simulated magnetic resonance image generated by the ring deep neural network.

In the embodiments of the present disclosure, through the pre-constructed first simulated magnetic resonance image class discrimination model, it is possible to discriminate whether or not the generated first simulated full-sampled magnetic resonance image is of a simulated magnetic resonance image class, and obtain a first discrimination result, thereby facilitate to feed back the first discrimination result to the training of the ring deep neural network through the preset loss function, so as to improve the quality of the simulated full-sampled magnetic resonance image generated by the first neural network of the ring deep neural network.

Step 15: inputting the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class.

The first simulated under-sampled magnetic resonance image here may be generated by Step 13. The under-sampled magnetic resonance image here may be acquired by Step 11.

In practical applications, the second neural network of the constructed ring deep neural network can also learn the mapping relationship from the full-sampled magnetic resonance image to the under-sampled magnetic resonance image. In order to improve the learning effect of the neural network, based on the same considerations as in Step 14, that is, the deviation between the first simulated under-sampled magnetic resonance image and the under-sampled magnetic resonance image that matches the full-sampled magnetic resonance image is fed back into the training of the ring deep neural network, which can improve the quality of the simulated magnetic resonance image generated by the ring deep neural network.

In the embodiments of the present disclosure, through the pre-constructed second simulated magnetic resonance image class discrimination model, it is possible to discriminate whether or not the generated first simulated under-sampled magnetic resonance image is of the simulated magnetic resonance image class, and obtain a second discrimination result, thereby facilitate to feed back the second discrimination result to the training of the ring deep neural network through a preset loss function, that is, the deviation existing between the first simulated under-sampled magnetic resonance image and the under-sampled magnetic resonance image is fed back into the training of the ring deep neural network.

In the embodiments of the present disclosure, the pre-constructed second simulated magnetic resonance image class discrimination model here may also be constructed based on convolutional neural network, for example, the second simulated magnetic resonance image class discrimination model may also adopt the network structure shown in FIG. 6. Of course, other types of neural network construction can also be used, which is not limited in the present disclosure.

In practical applications, in the training process of the ring deep neural network, in order to enable the second simulated magnetic resonance image class discrimination model to accurately output the second discrimination result, it can be understood that, making the second simulated magnetic resonance image class discrimination model as much as possible that the first simulated under-sampled magnetic resonance image is a simulated magnetic resonance image class, in one or more embodiments of the present disclosure, for the pre-constructed second simulated magnetic resonance image class discrimination model, the model parameters of the second simulated magnetic resonance image class discrimination model may be adjusted through a fifth loss function, so that the second simulated magnetic resonance image class discrimination model accurately outputs the second discrimination result.

The fifth loss function can be:

$$L_5 = \{E_y[\text{MSE}(D_s(G_{d-s}(y)), 1] + E_x[\text{MSE}(D_s(x), 0]\}/2$$

wherein, x represents the under-sampled magnetic resonance image, y represents the full-sampled magnetic resonance image, $G_{d\text{-}s}(y)$ represents the first simulated under-sampled magnetic resonance image, $D_s$ represents the second simulated magnetic resonance image class discrimination model, $D_s(G_{d\text{-}s}(y))$ represents the second discrimination result, $D_s(x)$ represents a result of class discrimination with respect to the under-sampled magnetic resonance image by the second simulated magnetic resonance image class discrimination model, $E_x$ represents a mathematical expectation of a first function whose input is the under-sampled magnetic resonance image, $E_y$ represents a mathematical expectation of a second function whose input is the full-sampled magnetic resonance image, and MSE represents a mean square error.

Adjusting the model parameters based on the fifth loss function may specifically comprising: calculating a loss value of the discrimination result of the second simulated magnetic resonance image class discrimination model through the fifth loss function, and feeding back the loss value to the second simulated magnetic resonance image class discrimination model by means of back propagation to adjust the model parameters.

In practical applications, since the input data of the second simulated magnetic resonance image class discrimination model comprises the first simulated under-sampled magnetic resonance image, and the first simulated under-sampled magnetic resonance image may be generated by the second neural network of the ring deep neural network, it can be considered that the second simulated magnetic resonance image class discrimination model and the ring deep neural network can be trained simultaneously. The training effects of the two are opposite, that is, training the ring deep neural network is expected to achieve the purpose of making the second simulated magnetic resonance image class discrimination model discriminate the first simulated under-sampled magnetic resonance image as a non-simulated magnetic resonance image class, while training the first simulated magnetic resonance image class discrimination model is expected to improve the accuracy of model discrimination, so as to discriminate the first simulated under-sampled magnetic resonance image as the simulated magnetic resonance image class as much as possible. Since the second discrimination result output by the second magnetic resonance image discrimination model can be fed back to the training of the ring deep neural network through the preset loss function, the discrimination accuracy of the second simulated magnetic resonance image class discrimination model can be improved, that is, the accuracy of the output second discrimination result can also be improved, also be equivalent to promoting the improvement of the quality of the simulated magnetic resonance image generated by the ring deep neural network.

In the embodiments of the present disclosure, through the pre-constructed second simulated magnetic resonance image class discrimination model, it is possible to discriminate whether or not the generated first simulated under-sampled magnetic resonance image is of a simulated magnetic resonance image class, and obtain a second discrimination result, thereby facilitate to feed back the second discrimination result to the training of the ring deep neural network through the preset loss function, so as to improve the quality of the simulated under-sampled magnetic resonance image generated by the second neural network of the ring deep neural network.

Step 16: adjusting a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

The first discrimination result and the second discrimination result here may be obtained by Step 14 and Step 15 respectively. The second simulated under-sampled magnetic resonance image and the second simulated full-sampled magnetic resonance image here may be generated by Step 13. The under-sampled magnetic resonance image and the full-sampled magnetic resonance image here may be acquired by Step 11. The ring deep neural network here can be constructed by Step 12.

In practical applications, to adjust the network parameters of the neural network, the loss value of the output result of the neural network can be calculated through the loss function, and then the loss value is fed back to the neural network through back propagation to adjust the network parameters. In one or more embodiments of the present disclosure, adjusting the network parameter of the ring deep neural network to obtain a trained magnetic resonance imaging model may specifically comprises:

obtaining a loss value by respectively substituting the first discrimination result, the second discrimination result, the second simulated under-sampled magnetic resonance image, the second simulated full-sampled magnetic resonance image, the under-sampled magnetic resonance image and the full-sampled magnetic resonance image into the preset loss function; and adjusting the network parameter based on the loss value.

In one or more embodiments of the present disclosure, the preset loss function may specifically comprises:

a first loss function for determining a first loss value based on the first discrimination result indicating whether or not the first simulated full-sampled magnetic resonance image is of a simulated magnetic resonance image class;

a second loss function for determining a second loss value based on the second discrimination result indicating whether or not the first simulated under-sampled magnetic resonance image is of the simulated magnetic resonance image class;

a third loss function for determining a third loss value based on a first mean absolute error between the second simulated full-sampled magnetic resonance image and the full-sampled magnetic resonance image, and based on a second mean absolute error between the second simulated under-sampled magnetic resonance image and the under-sampled magnetic resonance image.

In practical applications, obtaining a loss value by respectively substituting the first discrimination result, the second discrimination result, the second simulated under-sampled magnetic resonance image, the second simulated full-sampled magnetic resonance image, the under-sampled magnetic resonance image and the full-sampled magnetic resonance image into a preset loss function, may specifically comprises:

substituting the first discrimination result into the first loss function to obtain the first loss value;

substituting the second discrimination result into the second loss function to obtain the second loss value;

substituting the second simulated full-sampled magnetic resonance image, the full-sampled magnetic resonance image, the second simulated under-sampled magnetic resonance image and the under-sampled magnetic resonance image into the third loss function to obtain the third loss value.

In one or more embodiments of the present disclosure, the formulas of the first loss function, the second loss function and the third loss function may be respectively as follows:

the first loss function $L_1$ may be denoted as:

$$L_1 = E_x[\mathrm{MSE}(D_d(G_{s-d}(x)),1]$$

the second loss function $L_2$ may be denoted as:

$$L_2 = E_y[\mathrm{MSE}(D_s(G_{d-s}(y)),0]$$

the second loss function $L_3$ may be denoted as:

$$L_3 = E_x[\|x_{cir}-x\|_1] + E_y[\|y_{cir}-y\|_1]$$

wherein x represents the under-sampled magnetic resonance image, $G_{s-d}(x)$ represents the first simulated full-sampled magnetic resonance image, $D_d$ represents the first simulated magnetic resonance image class discrimination model, $D_d(G_{s-d}(x))$ represents the first discrimination result, MSE represents a mean square error function, and $E_x$ represents a mathematical expectation of a first function whose input is the under-sampled magnetic resonance image;

wherein y represents the full-sampled magnetic resonance image, $G_{d-s}(y)$ represents the first simulated under-sampled magnetic resonance image, $D_s$ represents the second simulated magnetic resonance image class discrimination model, $D_s(G_{d-s}(y))$ represents the second discrimination result, and $E_y$ represents a mathematical expectation of a second function whose input is the full-sampled magnetic resonance image;

wherein $x_{cir}$ represents the second simulated under-sampled magnetic resonance image, $y_{cir}$ represents the second simulated full-sampled magnetic resonance image, $\|x_{cir}-x\|_1$ represents the second mean absolute error, $\|y_{cir}-y\|_1$ represents the first mean absolute error.

In practical applications, the training effect of the neural network can be measured based on the size of the loss value of the loss function. Then, in the embodiments of the present disclosure, the training objective of the ring deep neural network may be to reduce the loss value of the preset loss function as much as possible. Then it can be considered that in the iterative training process of the ring deep neural network, by adjusting the network parameters, a trained ring deep neural network is obtained when the loss value of the preset loss function is lower than a preset value.

In practical applications, the generation of MRI images is usually to generate full-sampled image data from under-sampled image data. In the embodiments of the present disclosure, the trained magnetic resonance imaging model may be the first neural network of the trained magnetic resonance imaging model.

In the embodiments of the present disclosure, by means of the constructed ring deep neural network, during the process of training, not only the mapping relationship of the image generation direction from the under-sampled magnetic resonance image to the full-sampled magnetic resonance image can be learned, but also, since the addition of the second neural network in the opposite direction of the image generation, the mapping relationship in the opposite direction from the full-sampled magnetic resonance image to the under-sampled magnetic resonance image can also be learned, thereby the mapping relationship learned by the first neural network can be corrected, so that the first neural network can form a correct mapping in the desired image generation direction, thereby reducing the deviation between the generated MRI image and the actual MRI image, improving the quality of the MRI images generated by the magnetic resonance imaging model, and improving the learning ability and learning efficiency of the neural network.

On the other hand, by using the first simulated magnetic resonance image class discrimination model and the second simulated magnetic resonance image class discrimination model, the generated first simulated full-sampled magnetic resonance image and the first simulated under-sampled magnetic resonance image are also be discriminated, and the discrimination results are fed back to the training of the ring deep neural network through the loss function. It is expected to achieve the purpose of making the simulated magnetic resonance image discrimination model misjudge the simulated magnetic resonance image generated by the ring deep neural network as a non-simulated magnetic resonance image, so that the MM image generated by the trained magnetic resonance imaging model is as close as possible to the actual MRI image, thereby further improving the quality of the MM image generated by the magnetic resonance imaging model.

Figure 7:
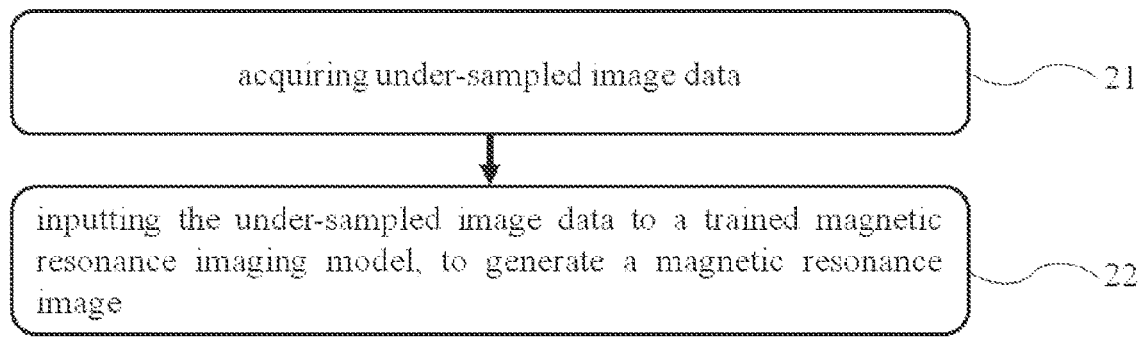
FIG. 7 is a schematic flowchart of a method for generating a magnetic resonance image according to an embodiment of the present disclosure.

The above is the training method for training the magnetic resonance imaging model provided by the embodiments of the present disclosure, and the embodiments of the present disclosure also provides a specific application scenario of the magnetic resonance imaging model trained by the training method for training of the magnetic resonance imaging model. The specific application scenario may be a method for generating a magnetic resonance image provided by the embodiments of the present disclosure, and the execution subject of the method may be a magnetic resonance imaging device, as shown in FIG. 7, the method for generating a magnetic resonance image specifically comprises the following steps:

Step 21, acquiring under-sampled image data.

In practical applications, the under-sampled image data here can be image data acquired by a magnetic resonance imaging device using a nuclear magnetic resonance phenomenon. It can be understood that the under-sampled image data here can be a certain amount of image data acquired by a magnetic resonance imaging device in order to reduce the time for image data acquisition.

In practical applications, the under-sampled image data can be collected by methods such as regular under-sampling based on partial k-space, random under-sampling based on Compressed Sensing (CS) theory, and Radial and Spiral under-sampling based on non-Cartesian sampling trajectories, etc., which is not limited in the present disclosure.

Step 22, inputting the under-sampled image data acquired in Step 21 to a trained magnetic resonance imaging model, to generate a magnetic resonance image.

In the embodiments of the present disclosure, the trained magnetic resonance imaging model may be obtained by, but is not limited to, training by using the method for training the magnetic resonance imaging model in the above-mentioned embodiments of the present disclosure. Wherein for the relevant description of the method for training the magnetic resonance imaging model, reference may be made to the content shown in the above-mentioned embodiments of the present disclosure, which will not be described here in order to avoid redundant description.

In practical applications, the under-sampled image data is input into the trained magnetic resonance imaging model, and high-quality MRI images can be generated by the trained magnetic resonance imaging model, facilitating clinical diagnosis.

With the method for generating a magnetic resonance image in the embodiments of the present disclosure, it is possible to generate high-quality MRI images based on collected under-sampled image data, especially by the magnetic resonance imaging model trained by the method for training a magnetic resonance imaging model in the above-mentioned embodiments of the present disclosure. Compared with the prior technology, the quality of the generated MM images can be further improved.

Figure 8:
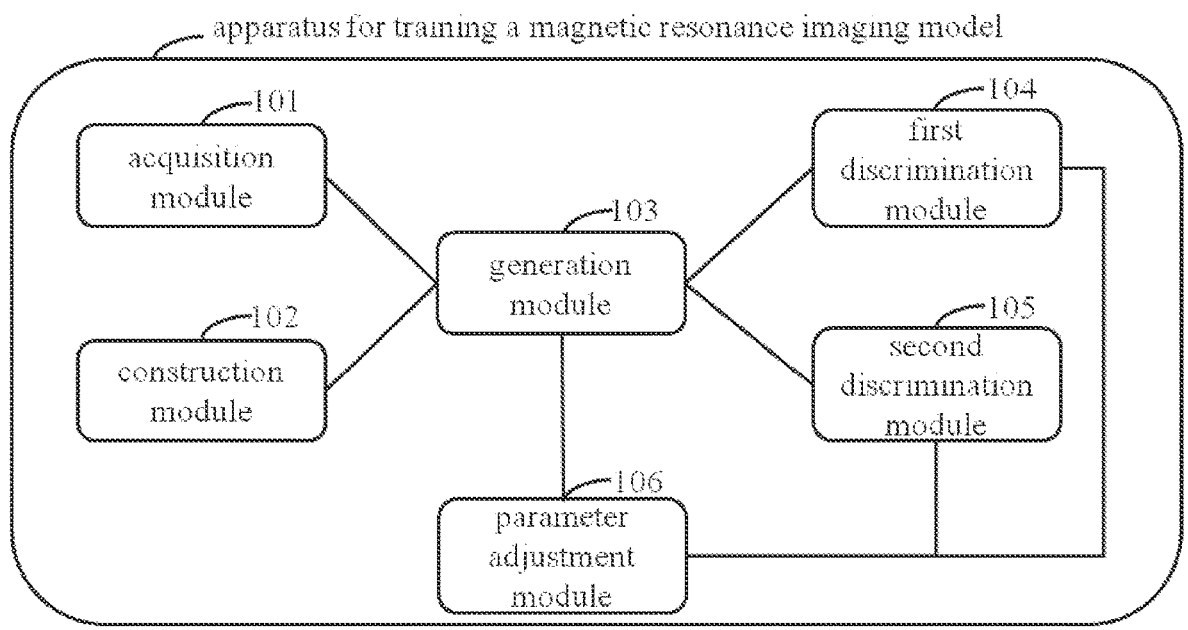
FIG. 8 is a schematic structure diagram of an apparatus for training a magnetic resonance imaging model according to an embodiment of the present disclosure.

The above is the method for training a magnetic resonance imaging model provided by the embodiments of the present disclosure, and the method for generating a magnetic resonance image based on the method for training a magnetic resonance imaging model. In the embodiments of the present disclosure, based on the same inventive concept as the method for training the magnetic resonance imaging model, a corresponding apparatus for training the magnetic resonance imaging model is also provided. As shown in FIG. 8, the apparatus specifically comprises:

an acquisition module 101, configured to acquire a magnetic resonance image data set comprising an under-sampled magnetic resonance image and a full-sampled magnetic resonance image;

a construction module 102, configured to construct a ring deep neural network to be trained, wherein the ring deep neural network comprises a first neural network at a first side, a second neural network at a second side, and two input ports respectively for the under-sampled magnetic resonance image and the full-sampled magnetic resonance image, wherein the first neural network is configured to generate a first simulated full-sampled magnetic resonance image based on the under-sampled magnetic resonance image and generate a second simulated full-sampled magnetic resonance image based on a first simulated under-sampled magnetic resonance image generated by the second neural network, and the second neural network is configured to generate the first simulated under-sampled magnetic resonance image based on the full-sampled magnetic resonance image and generate a second simulated under-sampled magnetic resonance image based on the first simulated full-sampled magnetic resonance image generated by the first neural network;

a generation module 103, configured to input the under-sampled magnetic resonance image and the full-sampled magnetic resonance image respectively to the first neural network and the second neural network via the two input ports, to generate respective simulated magnetic resonance images comprising the first simulated under-sampled magnetic resonance image, the first simulated full-sampled magnetic resonance image, the second simulated under-sampled magnetic resonance image and the second simulated full-sampled magnetic resonance image;

a first discrimination module 104, configured to input the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class;

a second discrimination module 105, configured to input the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class;

a parameter adjustment module 106, configured to adjust a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

The specific workflow of an embodiment of the above apparatus may comprise: an acquisition module 101, configured to acquire acquiring a magnetic resonance image data set, a construction module 102, configured to construct a ring deep neural network to be trained, a generation module 103, configured to input the under-sampled magnetic resonance image and the full-sampled magnetic resonance image respectively to the first neural network and the second neural network via the two input ports, to generate respective simulated magnetic resonance images, a first discrimination module 104, configured to input the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class, a second discrimination module 105, configured to input the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class, a parameter adjustment module 106, configured to adjust a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

In an implementation, the parameter adjustment module 106 specifically comprises:

a loss value calculation unit, configured to obtain a loss value by respectively substitute the first discrimination result, the second discrimination result, the second simulated under-sampled magnetic resonance image, the second simulated full-sampled magnetic resonance image, the under-sampled magnetic resonance image and the full-sampled magnetic resonance image into a preset loss function;

an adjustment unit, configured to adjust the network parameter based on the loss value, to obtain a trained magnetic resonance imaging model; the magnetic resonance imaging model comprises the first neural network of the ring deep neural network.

In an implementation, the first neural network of the ring deep neural network in the apparatus comprises a first down-sampling layer, a first residual network layer and a first up-sampling layer; and the second neural network comprises a second down-sampling layer, a second residual network layer and a second up-sampling layer;

the first down-sampling layer is configured to extract a first feature map of the under-sampled magnetic resonance image and extract a second feature map of the first simulated under-sampled magnetic resonance image;

the first residual network layer is configured to perform residual processing on the first feature map and the second feature map;

the first up-sampling layer is configured to generate the first simulated full-sampled magnetic resonance image based on the first feature map subjected to the residual processing, and generate the second simulated full-sampled magnetic resonance image based on the second feature map subjected to the residual processing;

the second down-sampling layer is configured to extract a third feature map of the full-sampled magnetic resonance image and extract a fourth feature map of the first simulated full-sampled magnetic resonance image;

the second residual network layer is configured to perform residual processing on the third feature map and the fourth feature map;

the second up-sampling layer is configured to generate the first simulated under-sampled magnetic resonance image based on the third feature map subjected to the residual processing and generate the second simulated under-sampled magnetic resonance image based on the fourth feature map subjected to the residual processing.

In an implementation, the preset loss function specifically comprises:

a first loss function for determining a first loss value based on the first discrimination result indicating whether or not the first simulated full-sampled magnetic resonance image is of a simulated magnetic resonance image class;

a second loss function for determining a second loss value based on the second discrimination result indicating whether or not the first simulated under-sampled magnetic resonance image is of the simulated magnetic resonance image class;

a third loss function for determining a third loss value based on a first mean absolute error between the second simulated full-sampled magnetic resonance image and the full-sampled magnetic resonance image and based on a second mean absolute error between the second simulated under-sampled magnetic resonance image and the under-sampled magnetic resonance image.

In an implementation, the first loss function $L_1$ is denoted as:

$$L_1 = E_x[\text{MSE}(D_d(G_{s\text{-}d}(x)), 1]$$

the second loss function $L_2$ is denoted as:

$$L_2 = E_y[\text{MSE}(D_s(G_{d\text{-}s}(y)), 0]$$

the third loss function $L_3$ is denoted as:

$$L_3 = E_x[\|x_{cir} - x\|_1] + E_y[\|y_{cir} - y\|_1]$$

wherein x represents the under-sampled magnetic resonance image, $G_{s\text{-}d}(x)$ represents the first simulated full-sampled magnetic resonance image, $D_d$ represents the first simulated magnetic resonance image class discrimination model, $D_d(G_{s\text{-}d}(x))$ represents the first discrimination result, MSE represents a mean square error function, and $E_x$ represents a mathematical expectation of a first function whose input is the under-sampled magnetic resonance image;

wherein y represents the full-sampled magnetic resonance image, $G_{d\text{-}s}(y)$ represents the first simulated under-sampled magnetic resonance image, $D_s$ represents the second simulated magnetic resonance image class discrimination model, $D_s(G_{d\text{-}s}(y))$ represents the second discrimination result, and $E_y$ represents a mathematical expectation of a second function whose input is the full-sampled magnetic resonance image;

wherein $x_{cir}$ represents the second simulated under-sampled magnetic resonance image, $y_{cir}$ represents the second simulated full-sampled magnetic resonance image, $\|x_{cir} - x\|_1$ represents the second mean absolute error, and $\|y_{cir} - y\|_1$ represents the first mean absolute error.

In an implementation, the apparatus further comprises:

a first model parameter adjustment module, configured to adjust a model parameter of the first simulated magnetic resonance image class discrimination model by a fourth loss function; the fourth loss function $L_4$ is denoted as:

$$L_4 = \{E_x[\text{MSE}(D_d(G_{s\text{-}d}(x)), 0] + E_y[\text{MSE}(D_d(y), 1]\}/2$$

a second model parameter adjustment module, configured to adjust a model parameter of the second simulated magnetic resonance image class discrimination model by a fifth loss function; the fifth loss function $L_4$ is denoted as:

$$L_5 = \{E_y[\text{MSE}(D_s(G_{d\text{-}s}(y)), 1] + E_x[\text{MSE}(D_s(x), 0]\}/2$$

wherein $D_d(y)$ represents a result of class discrimination with respect to the full-sampled magnetic resonance image by the first simulated magnetic resonance image class discrimination model, and $D_s(x)$ represents a result of class discrimination with respect to the under-sampled magnetic resonance image by the second simulated magnetic resonance image class discrimination model.

In the embodiments of the present disclosure, by means of the constructed ring deep neural network, during the process of training, not only the mapping relationship of the image generation direction from the under-sampled magnetic resonance image to the full-sampled magnetic resonance image can be learned, but also, since the addition of the second neural network in the opposite direction of the image generation, the mapping relationship in the opposite direction from the full-sampled magnetic resonance image to the under-sampled magnetic resonance image can also be learned, thereby the mapping relationship learned by the first neural network can be corrected, so that the first neural network can form a correct mapping in the desired image generation direction, thereby reducing the deviation between the generated MM image and the actual MRI image, improving the quality of the MRI images generated by the magnetic resonance imaging model, and improving the learning ability and learning efficiency of the neural network.

On the other hand, by using the first simulated magnetic resonance image class discrimination model and the second simulated magnetic resonance image class discrimination model, the generated first simulated full-sampled magnetic resonance image and the first simulated under-sampled magnetic resonance image are also be discriminated, and the discrimination results are fed back to the training of the ring deep neural network through the loss function. It is expected to achieve the purpose of making the simulated magnetic resonance image discrimination model misjudge the simulated magnetic resonance image generated by the ring deep neural network as a non-simulated magnetic resonance image, so that the MRI image generated by the trained magnetic resonance imaging model is as close as possible to the actual MRI image, thereby further improving the quality of the MM image generated by the magnetic resonance imaging model.

Figure 9:
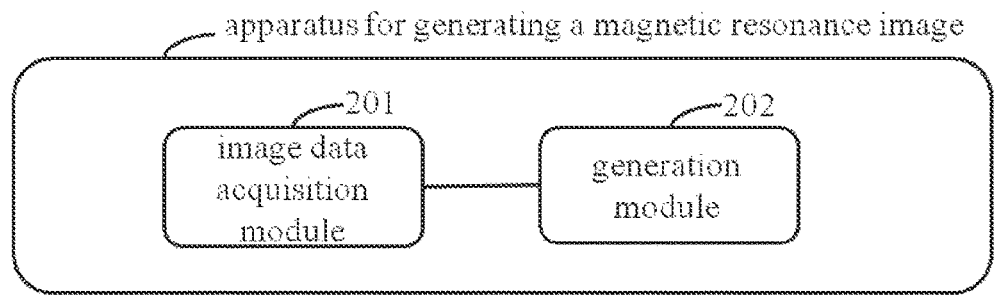
FIG. 9 is a schematic structure diagram of an apparatus for generating a magnetic resonance image according to an embodiment of the present disclosure.

Based on the same inventive concept as the above-mentioned method for generating a magnetic resonance image, the embodiments of the present disclosure further provides an apparatus for generating a magnetic resonance image, as shown in FIG. 9, the apparatus specifically comprises:

an image data acquisition module 201, configured to acquire under-sampled image data;

a generation module 202, configured to input the under-sampled image data to the trained magnetic resonance imaging model, to generate a magnetic resonance image.

The specific workflow of an embodiment of the above apparatus for generating a magnetic resonance image may comprise: an image data acquisition module 201, configured to acquire under-sampled image data, a generation module 202, configured to input the under-sampled image data acquired by the image data acquisition module 201 to a trained magnetic resonance imaging model, to generate a magnetic resonance image.

With the apparatus for generating a magnetic resonance image in the embodiments of the present disclosure, it is possible to generate high-quality MRI images based on a small amount of collected image data, especially by the magnetic resonance imaging model trained by the method for training a magnetic resonance imaging model in the above-mentioned embodiments of the present disclosure. Compared with the prior technology, the quality of the generated MRI image can be further improved.

Figure 10:
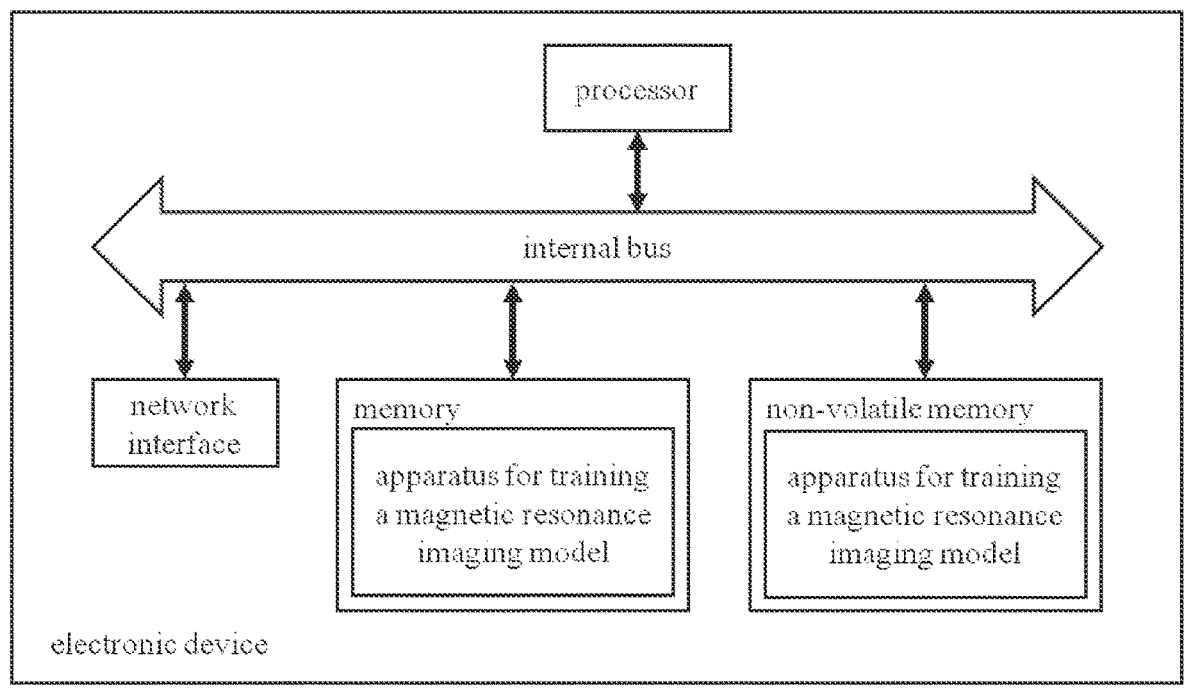
FIG. 10 is a schematic structure diagram of an electronic device according to an embodiment of the present disclosure.

The embodiments of the present disclosure also provide an electronic device, please refer to FIG. 10 for a schematic diagram, at the hardware level, the electronic device comprises a processor, and optionally an internal bus, a network interface, and a storage. Wherein, the storage may comprise a memory, such as a high-speed random-access memory (RAM), and may also comprise a non-volatile memory, such as at least one disk memory. Of course, the electronic device may also comprise hardware required for other services.

The processor, network interface, and storage can be connected to each other through the internal bus, which can be an ISA (Industry Standard Architecture) bus, a PCI (Peripheral Component Interconnect) bus, and an EISA (Extended Industry Standard Architecture) bus, etc. The bus can be divided into an address bus, a data bus, a control bus, and the like. For ease of representation, only one bidirectional arrow is shown in FIG. 10, but it does not mean that there is only one bus and one type of bus.

The storage is configured to store a program. Specifically, the program may comprise program code, and the program code comprises computer operation instructions. The storage may comprise a memory and a non-volatile memory and provide instructions and data to the processor.

The processor reads the corresponding computer program from the non-volatile memory into the memory and then executes it, forming a training apparatus for applying the magnetic resonance imaging model on a logical level. The processor executes the program stored in the memory and is used to perform at least the following operations:

acquiring a magnetic resonance image data set comprising an under-sampled magnetic resonance image and a full-sampled magnetic resonance image;

constructing a ring deep neural network to be trained; wherein the ring deep neural network comprises a first neural network at a first side, a second neural network at a second side, and two input ports respectively for the under-sampled magnetic resonance image and the full-sampled magnetic resonance image;

the first neural network is configured to generate a first simulated full-sampled magnetic resonance image based on the under-sampled magnetic resonance image and generate a second simulated full-sampled magnetic resonance image based on a first simulated under-sampled magnetic resonance image generated by the second neural network; the second neural network is configured to generate the first simulated under-sampled magnetic resonance image based on the full-sampled magnetic resonance image and generate a second simulated under-sampled magnetic resonance image based on the first simulated full-sampled magnetic resonance image generated by the first neural network;

inputting the under-sampled magnetic resonance image and the full-sampled magnetic resonance image respectively to the first neural network and the second neural network via the two input ports, to generate respective simulated magnetic resonance images comprising the first simulated under-sampled magnetic resonance image, the first simulated full-sampled magnetic resonance image, the second simulated under-sampled magnetic resonance image and the second simulated full-sampled magnetic resonance image;

inputting the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class;

inputting the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class;

adjusting a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

The above-mentioned method, disclosed in the embodiment shown in FIG. 1 of the present disclosure and performed by the apparatus for training a magnetic resonance imaging model disclosed in the embodiment shown in FIG. 1 of the present application may be applied to a processor, or implemented by a processor. The processor may be an integrated circuit chip with signal processing capabilities. In the implementation process, each step of the above method can be completed by hardware integrated logic circuits in the processor or instructions in the form of software. The above-mentioned processor may be a general-purpose processor, including a Central Processing Unit (CPU), a Network Processor (NP), etc.; it may also be a Digital Signal Processor (DSP), Application Specific Integrated Circuit (ASIC), Field-Programmable Gate Array (FPGA) and other programmable logic devices, discrete gates or transistor logic devices, discrete hardware components. Various methods, steps and logic block diagrams disclosed in the embodiments of the present disclosure can be implemented or executed. A general purpose processor may be a microprocessor or the processor may be any conventional processor or the like. The steps of the method disclosed in conjunction with the embodiments of the present disclosure can be directly embodied as being executed by a hardware decoding processor, or by a combination of hardware and software modules in the decoding processor. The software modules may be located in random access memory, flash memory, read-only memory, programmable read-only memory, or electrically erasable programmable memory, registers and other storage media mature in the art. The storage medium is located in the storage, and the processor reads the information in the storage, and completes the steps of the above method in combination with its hardware.

The electronic device can also execute the method performed by the apparatus for training the magnetic resonance imaging model in FIG. 1, and realize the functions of the apparatus for training the magnetic resonance imaging model in the embodiment shown in FIG. 1, which will not be repeated here.

The embodiments of the present disclosure also provide a computer-readable storage medium that stores one or more programs including instructions, which when executed by an electronic device including multiple application programs, cause the electronic device to perform the method executed by the apparatus for training the magnetic resonance imaging model in the embodiment shown in FIG. 1, and at least configured to perform:

acquiring a magnetic resonance image data set comprising an under-sampled magnetic resonance image and a full-sampled magnetic resonance image;

constructing a ring deep neural network to be trained; wherein the ring deep neural network comprises a first neural network at a first side, a second neural network at a second side, and two input ports respectively for the under-sampled magnetic resonance image and the full-sampled magnetic resonance image;

the first neural network is configured to generate a first simulated full-sampled magnetic resonance image based on the under-sampled magnetic resonance image and generate a second simulated full-sampled magnetic resonance image based on the first simulated under-sampled magnetic resonance image generated by the second neural network; the second neural network is configured to generate the first simulated under-sampled magnetic resonance image based on the full-sampled magnetic resonance image and generate a second simulated under-sampled magnetic resonance image based on the first simulated full-sampled magnetic resonance image generated by the first neural network;

inputting the under-sampled magnetic resonance image and the full-sampled magnetic resonance image respectively to the first neural network and the second neural network via the two input ports, to generate respective simulated magnetic resonance images comprising the first simulated under-sampled magnetic resonance image, the first simulated full-sampled magnetic resonance image, the second simulated under-sampled magnetic resonance image and the second simulated full-sampled magnetic resonance image;

inputting the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class;

inputting the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class;

adjusting a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

As will be appreciated by those skilled in the art, the embodiments of the present disclosure may be provided as methods, systems, and computer program products. Accordingly, the present disclosure may take the form of an entirely hardware embodiment, an entirely software embodiment, and an embodiment combining software and hardware aspects. Furthermore, the present disclosure may take the form of a computer program product embodied on one or more computer-usable storage media (including, but not limited to, disk storage, CD-ROM, optical storage, etc.) comprising computer-usable program code.

The present disclosure is described with reference to flowchart illustrations and/or block diagrams of methods, apparatuses (systems), and computer program products based on embodiments of the present disclosure. It will be understood that each flow and/or block in the flowcharts and/or block diagrams, and combinations of flows and/or blocks in the flowcharts and/or block diagrams, can be implemented by computer program instructions. These computer program instructions may be provided to the processors of general purpose computers, special purpose computers, embedded processors and other programmable data processing devices to produce a machine such that the instructions executed by the processors of computers and other programmable data processing devices produce apparatus for implementing the functions specified in one or more flows of the flowcharts and/or one or more blocks of the block diagrams.

These computer program instructions may also be stored in a computer-readable memory capable of directing computers and other programmable data processing devices to operate in a particular manner, such that instructions stored in the computer-readable memory to produce an article of manufacture comprising instruction apparatus, which implements the functions specified in one or more flows of the flowcharts and/or one or more blocks of the block diagrams.

These computer program instructions can also be loaded on computers and other programmable data processing devices to cause a series of operational steps to be performed on the computer and other programmable devices to produce a computer-implemented process, whereby the instructions executed on the computers and other programmable devices provide for implementing the steps of the functions specified in one or more flows of the flowcharts and/or one or more blocks of the block diagrams.

In a typical configuration, a computing device comprises one or more processors (CPUs), input/output interfaces, network interfaces, and memories.

The memories may comprise the form of non-persistent storage, random access memory (RAM) and/or non-volatile memory in computer readable media, such as read only memory (ROM) and flash memory (flash RAM). Memory is an example of a computer-readable medium.

The computer-readable media, including persistent and non-permanent, removable and non-removable media, can be implemented by any method or technology for information storage. Information may be computer readable instructions, data structures, modules of programs, and other data. Examples of computer storage media include, but are not limited to, phase-change memory (PRAM), static random access memory (SRAM), dynamic random access memory (DRAM), other types of random access memory (RAM), read only memory (ROM), Electrically Erasable Programmable Read Only Memory (EEPROM), Flash Memory and other memory technologies, Compact Disc Read Only Memory (CD-ROM), Digital Versatile Disc (DVD) and other optical storage, magnetic cassettes, magnetic disk tape storage and other magnetic storage devices and any other non-transmission media that can be used to store information that can be accessed by computing devices. As defined herein, computer-readable media does not include computer-readable transitory media, such as modulated data signals and carrier waves.

It should also be noted that the terms "include", "comprise" and/or any other variations thereof are intended to encompass a non-exclusive inclusion, such that a process, method, article and/or device comprising a series of elements includes not only those elements, but also other elements not expressly listed or inherent to such a process, method, article and/or device. Without further limitation, an element defined by the phrase "comprise a . . . " does not preclude the presence of additional identical elements in the process, method, article and/or device that includes the element.

The above are merely examples of the present disclosure, and are not intended to limit the present disclosure. Various modifications and variations may be made by those skilled in the art based on the present disclosure. Any modification, equivalent replacement, improvement, or the like made within the spirit and principle of the present disclosure shall fall in the scope of the claims of the present disclosure.

The invention claimed is:

1. A method for training a magnetic resonance imaging model, comprising:
   acquiring a magnetic resonance image data set comprising an under-sampled magnetic resonance image and a full-sampled magnetic resonance image;
   constructing a ring deep neural network to be trained, wherein the ring deep neural network comprises a first neural network at a first side, a second neural network at a second side, and two input ports respectively for the under-sampled magnetic resonance image and the full-sampled magnetic resonance image, wherein the first neural network is configured to generate a first simulated full-sampled magnetic resonance image based on the under-sampled magnetic resonance image and generate a second simulated full-sampled magnetic resonance image based on a first simulated under-sampled magnetic resonance image generated by the second neural network, and the second neural network is configured to generate the first simulated under-sampled magnetic resonance image based on the full-sampled magnetic resonance image and generate a second simulated under-sampled magnetic resonance image based on the first simulated full-sampled magnetic resonance image generated by the first neural network;
   inputting the under-sampled magnetic resonance image and the full-sampled magnetic resonance image respectively to the first neural network and the second neural network via the two input ports, to generate respective simulated magnetic resonance images comprising the first simulated under-sampled magnetic resonance image, the first simulated full-sampled magnetic resonance image, the second simulated under-sampled magnetic resonance image and the second simulated full-sampled magnetic resonance image;
   inputting the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class;
   inputting the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class; and
   adjusting a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

2. The method of claim 1, wherein the adjusting of the network parameter comprises:
   obtaining a loss value by respectively substituting the first discrimination result, the second discrimination result, the second simulated under-sampled magnetic resonance image, the second simulated full-sampled magnetic resonance image, the under-sampled magnetic resonance image and the full-sampled magnetic resonance image into the preset loss function; and
   adjusting the network parameter based on the loss value.

3. The method of claim 1, wherein
   the first neural network comprises a first down-sampling layer, a first residual network layer and a first up-sampling layer, and the second neural network comprises a second down-sampling layer, a second residual network layer and a second up-sampling layer;
   the first down-sampling layer is configured to extract a first feature map of the under-sampled magnetic resonance image and extract a second feature map of the first simulated under-sampled magnetic resonance image;

the first residual network layer is configured to perform residual processing on the first feature map and the second feature map;

the first up-sampling layer is configured to generate the first simulated full-sampled magnetic resonance image based on the first feature map subjected to the residual processing and generate the second simulated full-sampled magnetic resonance image based on the second feature map subjected to the residual processing;

the second down-sampling layer is configured to extract a third feature map of the full-sampled magnetic resonance image and extract a fourth feature map of the first simulated full-sampled magnetic resonance image;

the second residual network layer is configured to perform residual processing on the third feature map and the fourth feature map; and the second up-sampling layer is configured to generate the first simulated under-sampled magnetic resonance image based on the third feature map subjected to the residual processing and generate the second simulated under-sampled magnetic resonance image based on the fourth feature map subjected to the residual processing.

4. The method of claim 1, wherein the preset loss function comprises:

a first loss function for determining a first loss value based on the first discrimination result;

a second loss function for determining a second loss value based on the second discrimination result; and a third loss function for determining a third loss value based on a first mean absolute error between the second simulated full-sampled magnetic resonance image and the full-sampled magnetic resonance image and based on a second mean absolute error between the second simulated under-sampled magnetic resonance image and the under-sampled magnetic resonance image.

5. The method of claim 4, wherein
the first loss function is denoted as $$\mathcal{L}_1 = E_x[\mathrm{MSE}(D_d(G_{s\text{-}d}(x)),1)],$$

the second loss function is denoted as $$\mathcal{L}_2 = E_y[\mathrm{MSE}(D_s(G_{d\text{-}s}(y)),0)],$$

the third loss function is denoted as $$\mathcal{L}_3 = E_x[\|x_{cir}-x\|_1] + E_y[\|y_{cir}-y\|_1],$$

wherein x represents the under-sampled magnetic resonance image, $G_{s\text{-}d}(x)$ represents the first simulated full-sampled magnetic resonance image, $D_d$ represents the first simulated magnetic resonance image class discrimination model, $D_d(G_{s\text{-}d}(x))$ represents the first discrimination result, MSE represents a mean square error function, and $E_x$ represents a mathematical expectation of a first function whose input is the under-sampled magnetic resonance image;

wherein y represents the full-sampled magnetic resonance image, $G_{d\text{-}s}(y)$ represents the first simulated under-sampled magnetic resonance image, $D_s$ represents the second simulated magnetic resonance image class discrimination model, $D_s(G_{d\text{-}s}(y))$ represents the second discrimination result, and $E_y$ represents a mathematical expectation of a second function whose input is the full-sampled magnetic resonance image;

wherein $x_{cir}$ represents the second simulated under-sampled magnetic resonance image, $y_{cir}$ represents the second simulated full-sampled magnetic resonance image, $\|x_{cir}-x\|_1$ represents the second mean absolute error, and $\|y_{cir}-y\|_1$ represents the first mean absolute error.

6. The method of claim 1, further comprising:

adjusting a model parameter of the first simulated magnetic resonance image class discrimination model by a fourth loss function denoted as $$\mathcal{L}_4 = \{E_x[\mathrm{MSE}(D_d(G_{s\text{-}d}(x)),0)] + E_y[\mathrm{MSE}(D_d(y),1)]\}/2; \text{ and}$$

adjusting a model parameter of the second simulated magnetic resonance image class discrimination model by a fifth loss function denoted as $$\mathcal{L}_5 = \{E_y[\mathrm{MSE}(D_s(G_{d\text{-}s}(y)),1)] + E_x[\mathrm{MSE}(D_s(x),0)]\}/2,$$

wherein $D_d(y)$ represents a result of class discrimination with respect to the full-sampled magnetic resonance image by the first simulated magnetic resonance image class discrimination model, and $D_s(x)$ represents a result of class discrimination with respect to the under-sampled magnetic resonance image by the second simulated magnetic resonance image class discrimination model.

7. A method for generating a magnetic resonance image, comprising:

acquiring under-sampled image data; and inputting the under-sampled image data to a magnetic resonance imaging model trained by the method of claim 1, to generate a magnetic resonance image.

8. An electronic device, comprising:

one or more processors; and a non-transitory memory, wherein the memory stores a computer program executable by the one or more processors to perform operations comprising:

acquiring a magnetic resonance image data set comprising an under-sampled magnetic resonance image and a full-sampled magnetic resonance image;

constructing a ring deep neural network to be trained, wherein the ring deep neural network comprises a first neural network at a first side, a second neural network at a second side, and two input ports respectively for the under-sampled magnetic resonance image and the full-sampled magnetic resonance image, wherein the first neural network is configured to generate a first simulated full-sampled magnetic resonance image based on the under-sampled magnetic resonance image and generate a second simulated full-sampled magnetic resonance image based on a first simulated under-sampled magnetic resonance image generated by the second neural network, and the second neural network is configured to generate the first simulated under-sampled magnetic resonance image based on the full-sampled magnetic resonance image and generate a second simulated under-sampled magnetic resonance image based on the first simulated full-sampled magnetic resonance image generated by the first neural network;

inputting the under-sampled magnetic resonance image and the full-sampled magnetic resonance image respectively to the first neural network and the second neural network via the two input ports, to generate respective simulated magnetic resonance images comprising the first simulated under-sampled magnetic resonance image, the first simulated full-sampled magnetic resonance image, the second simulated under-sampled magnetic resonance image and the second simulated full-sampled magnetic resonance image;

inputting the first simulated full-sampled magnetic resonance image and the full-sampled magnetic resonance image to a pre-constructed first simulated magnetic resonance image class discrimination model, to obtain a first discrimination result indicating whether or not the first simulated full-sampled magnetic resonance image is of a simulated magnetic resonance image class;

inputting the first simulated under-sampled magnetic resonance image and the under-sampled magnetic resonance image to a pre-constructed second simulated magnetic resonance image class discrimination model, to obtain a second discrimination result indicating whether or not the first simulated under-sampled magnetic resonance image is of the simulated magnetic resonance image class; and adjusting a network parameter of the ring deep neural network based on a preset loss function, the first discrimination result, the second discrimination result, the second simulated under-sampled magnetic resonance image, the second simulated full-sampled magnetic resonance image, the under-sampled magnetic resonance image and the full-sampled magnetic resonance image, to obtain a trained magnetic resonance imaging model.

9. The electronic device of claim 8, wherein the adjusting of the network parameter comprises:

obtaining a loss value by respectively substituting the first discrimination result, the second discrimination result, the second simulated under-sampled magnetic resonance image, the second simulated full-sampled magnetic resonance image, the under-sampled magnetic resonance image and the full-sampled magnetic resonance image into the preset loss function; and adjusting the network parameter based on the loss value.

10. The electronic device of claim 8, wherein the first neural network comprises a first down-sampling layer, a first residual network layer and a first up-sampling layer, and the second neural network comprises a second down-sampling layer, a second residual network layer and a second up-sampling layer;

the first down-sampling layer is configured to extract a first feature map of the under-sampled magnetic resonance image and extract a second feature map of the first simulated under-sampled magnetic resonance image;

the first residual network layer is configured to perform residual processing on the first feature map and the second feature map;

the first up-sampling layer is configured to generate the first simulated full-sampled magnetic resonance image based on the first feature map subjected to the residual processing and generate the second simulated full-sampled magnetic resonance image based on the second feature map subjected to the residual processing;

the second down-sampling layer is configured to extract a third feature map of the full-sampled magnetic resonance image and extract a fourth feature map of the first simulated full-sampled magnetic resonance image;

the second residual network layer is configured to perform residual processing on the third feature map and the fourth feature map; and the second up-sampling layer is configured to generate the first simulated under-sampled magnetic resonance image based on the third feature map subjected to the residual processing and generate the second simulated under-sampled magnetic resonance image based on the fourth feature map subjected to the residual processing.

11. The electronic device of claim 8, wherein the preset loss function comprises:

a first loss function for determining a first loss value based on the first discrimination result;

a second loss function for determining a second loss value based on the second discrimination result; and a third loss function for determining a third loss value based on a first mean absolute error between the second simulated full-sampled magnetic resonance image and the full-sampled magnetic resonance image and based on a second mean absolute error between the second simulated under-sampled magnetic resonance image and the under-sampled magnetic resonance image.

12. The electronic device of claim 11, wherein the first loss function is denoted as $\mathcal{L}_1 = E_x[\mathrm{MSE}(D_d(G_{s\text{-}d}(x)),1)]$, the second loss function is denoted as $\mathcal{L}_2 = E_y[\mathrm{MSE}(D_s(G_{d\text{-}s}(y)),0)]$, the third loss function is denoted as $\mathcal{L}_3 = E_x[\|x_{cir}-x\|_1] + E_y[\|y_{cir}-y\|_1]$, wherein x represents the under-sampled magnetic resonance image, $G_{s\text{-}d}(x)$ represents the first simulated full-sampled magnetic resonance image, $D_d$ represents the first simulated magnetic resonance image class discrimination model, $D_d(G_{s\text{-}d}(x))$ represents the first discrimination result, MSE represents a mean square error function, and $E_x$ represents a mathematical expectation of a first function whose input is the under-sampled magnetic resonance image;

wherein y represents the full-sampled magnetic resonance image, $G_{d\text{-}s}(y)$ represents the first simulated under-sampled magnetic resonance image, $D_s$ represents the second simulated magnetic resonance image class discrimination model, $D_s(G_{d\text{-}s}(y))$ represents the second discrimination result, and $E_y$ represents a mathematical expectation of a second function whose input is the full-sampled magnetic resonance image; and wherein $x_{cir}$ represents the second simulated under-sampled magnetic resonance image, $y_{cir}$ represents the second simulated full-sampled magnetic resonance image, $\|x_{cir}-x\|_1$ represents the second mean absolute error, and $\|y_{cir}-y\|_1$ represents the first mean absolute error.

13. The electronic device of claim 8, wherein the operations further comprise:

adjusting a model parameter of the first simulated magnetic resonance image class discrimination model by a fourth loss function denoted as $\mathcal{L}_4 = \{E_x[\mathrm{MSE}(D_d(G_{s\text{-}d}(x)),0)] + E_y[\mathrm{MSE}(D_d(y),1)]\}/2$; and adjusting a model parameter of the second simulated magnetic resonance image class discrimination model by a fifth loss function denoted as $\mathcal{L}_5 = \{E_y[\mathrm{MSE}(D_s(G_{d\text{-}s}(y)),1)] + E_x[\mathrm{MSE}(D_s(x),0)]\}/2$, wherein $D_d(y)$ represents a result of class discrimination with respect to the full-sampled magnetic resonance image by the first simulated magnetic resonance image class discrimination model, and $D_s(x)$ represents a result of class discrimination with respect to the under-sampled magnetic resonance image by the second simulated magnetic resonance image class discrimination model.

14. An electronic device, comprising:

one or more processors; and a non-transitory memory, wherein the memory stores a computer program executable by the one or more processors to perform operations comprising:
acquiring under-sampled image data; and
inputting the under-sampled image data to a magnetic resonance imaging model trained by the method of claim 1, to generate a magnetic resonance image.

\* \* \* \* \*